United States Patent [19]

White

[11] Patent Number: 5,108,397

[45] Date of Patent: Apr. 28, 1992

[54] METHOD AND APPARATUS FOR STABILIZATION OF PELVIC FRACTURES

[76] Inventor: Joseph White, 8463 Brook Rd., McLean, Va. 22102

[21] Appl. No.: 511,254

[22] Filed: Apr. 19, 1990

[51] Int. Cl.$^5$ .............................................. A61B 17/58
[52] U.S. Cl. ...................................... 606/60; 606/70; 606/73
[58] Field of Search .................. 606/60, 69, 70, 71, 606/72, 74, 75, 103, 73; 411/371

[56] References Cited

U.S. PATENT DOCUMENTS

| | | | |
|---|---|---|---|
| 2,501,978 | 3/1950 | Wichman | 606/74 X |
| 2,502,902 | 4/1950 | Tofflemire | 606/74 X |
| 4,454,876 | 6/1984 | Mears | 606/69 |
| 4,456,006 | 6/1984 | Wevers et al. | 606/75 |
| 4,651,724 | 3/1987 | Berentey et al. | 606/69 |
| 4,800,874 | 1/1989 | David et al. | 606/69 |
| 4,988,350 | 1/1991 | Herzberg | 606/71 X |

FOREIGN PATENT DOCUMENTS

| | | | |
|---|---|---|---|
| 3817783 | 12/1989 | Fed. Rep. of Germany | 411/371 |
| 67552 | 3/1944 | Norway | 606/69 |
| 1367961 | 1/1988 | U.S.S.R. | 606/60 |

OTHER PUBLICATIONS

Tile, Marvin: "Pelvis Ring Fractures: Should They Be Fixed?"; The Journal of Bone and Joint Surgery, vol. 70-B, No. 1, Jan. 1988, pp. 1–12.

Lange, Richard H.; Hansen, Jr., Sigvard T., Hansen, Jr., "Pelvic Ring Distruptions with Symphysis Pubis Diastasis": Clinical Orthopaedics and Related Research; No. 201, Dec. 1985, pp. 130–137.

Mears & Rubash, Pelvic and Acetabllerar Fractures, N. J., Slack Pubs. 1986, pp. 220–221.

Primary Examiner—Robert A. Hafer
Assistant Examiner—Kevin G. Rooney
Attorney, Agent, or Firm—Sherman and Shalloway

[57] ABSTRACT

A method and apparatus for stabilization of pelvic fractures, and particularly double vertical fractures, that provides for accurate restoration of the anterior and posterior integrity of the pelvic ring. The method involves rigid fixation of a posterior fracture with a plate and rod apparatus that applies rigid compression through the wings of the ilium and across the sacrum at the correct angle and non-rigid fixation across the anterior pubic symphysis with a screw and cable apparatus that applies flexible compression.

13 Claims, 3 Drawing Sheets

METHOD AND APPARATUS FOR STABILIZATION OF PELVIC FRACTURES

BACKGROUND OF THE INVENTION

The present invention is directed toward a method and apparatus for the stabilization of pelvic fractures, particularly unstable fractures such as those referred to as Malgaigne fractures which involve fractures or dislocations of both the ilium or sacroiliac joint and the pubis or pubic symphysis. These fractures are vertically oriented and completely disrupt the integrity of the pelvic ring, thus permitting one-half of the pelvis to move in relation to the opposite half. Examples of these fractures include fracture of both the inferior and superior pubic ramus coupled with an ipsilateral sacroiliac dislocation; dislocation of the pubic symphysis in conjunction with a sacroiliac dislocation; and symphyseal dislocation with fracture of the ilium.

Stabilization of such fractures requires restoring the internal integrity anteriorly at the symphysis pubis and posteriorly across the ilium or the sacroiliac joint. Prior methods of posterior stabilization have involved the use of screws across the sacroiliac joint into the sacrum directly, a plate which bridges between the two iliac bones at the level of the posterior superior iliac spine and Harrington compression rods which traverse the iliac wings.

Although effective in certain instances, each of these prior methods and apparatus have distinct limitations and disadvantages.

In the case of sacral screws, that is screws passing directly from the ilium to the sacrum across the sacroiliac joint, the blind passage of these screws can damage structures in the sacrum or, if the sacrum is missed, the screws can damage the viscera in the pelvic brim. Furthermore, if the sacrum itself is fractured, it is difficult to get the correct screw length, again due to it being a blind passage.

The disadvantage of plate fixation is two fold; the variation in pelvic sizes requires several different sizes of plates, and, even when the correct size is used, the plates tend to hold the pelvic bones apart, that is in distraction, which does not promote bone healing but may cause a non-union to develop. In contrast to the plate, Harrington compression rods squeeze the fracture together which does promote healing; but they may cause the fracture to open anteriorly because there is no fixed relationship between the rod and the washer which actually compresses the fractures. This problem occurs in the transverse plane when compression is applied posteriorly causing the anterior of the symphysis pubis to open. In the coronal plane, since there is no fixation between the rod and the washer, a condition known as toggle can develop allowing one side of the pelvis to ride up and down relative to the opposite side.

Accordingly, it is an object of this invention to provide a method and apparatus for the stabilization of pelvic fractures that overcomes the disadvantages of the prior methods and apparatus. It is a further object to provide a further method and apparatus for the stabilization of pelvic fractures that provides rigid posterior fixation while maintaining anterior flexibility. It is a still further object to provide a method and apparatus for the stabilization of pelvic fractures that provides for rigid, non-wobbling posterior fixation.

SUMMARY OF THE INVENTION

The objectives are achieved through the use of a combination of a rod and plate apparatus for application of rigid compression to the posterior fracture and a screw and cable apparatus for flexible compression or fixation of the anterior fracture. The rod and plate combination is employed in a manner similar to that of Harrington compression rods but is unique in that the construction of the plate maintains the rods in a parallel configuration and provides for a fixed relationship of the rods with the plates thereby eliminating any wobble. Additionally, the use of the separate plate and rod combination eliminates the need to keep several sizes of bridge type plates on hand. The screw and cable apparatus is used for anterior fractures, particularly fractures and dislocations across the pubic symphysis. This apparatus provides the necessary compression or fixation while maintaining flexibility in this portion of the pelvis during surgery on the posterior ring. Prior methods stabilized the pubic symphysis with a rigid plate which made subsequent accurate relocation and fixation of the posterior pelvis difficult.

The respective apparatus may be used separately for treatment of single fractures and dislocations of the posterior or anterior pelvis but are particularly effective when used in combination for the treatment and stabilization of double vertical fractures as hereinafter disclosed.

BRIEF DESCRIPTION OF THE DRAWING FIGURES

DETAILED DESCRIPTION OF THE INVENTION

Figure 1:
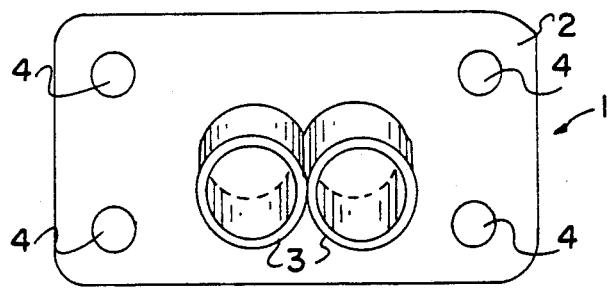
FIG. 1 is a vertical view of the plate apparatus of this invention.
Figure 2:
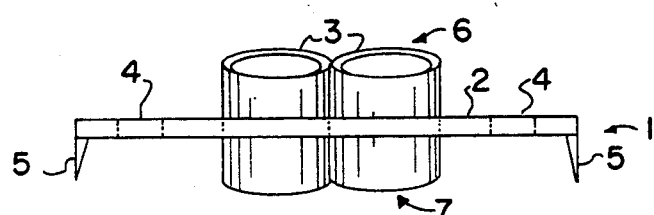
FIG. 2 is a horizontal view of the plate apparatus of this invention.
Figure 3:
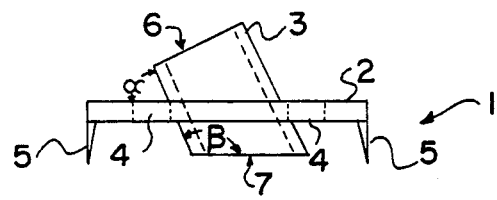
FIG. 3 is a horizontal view of the plate apparatus of this invention from one end thereof.

Referring to FIGS. 1 through 3, the plate and rod apparatus of this invention has, as its principle component, a plate member 1 comprising a substantially planar rectangular plate section 2 and a pair of parallel hollow cylinders 3. The plate section 2 is approximately 3 cm by 4 cm with a thickness of 0.5 cm and is made of a biocompatible material of sufficient rigidity to withstand deformation under stress. Such materials include stainless steel, Vitallium, titanium or other biocompatible metals and alloys. Apertures 4 are provided in the plate section 2 for fixation of the plate member by means of cortical bone screws. Additionally, the underside of the plate section 2 is provided with spikes or spines 5 at each corner of the rectangular plate section which extend perpendicularly from the undersurface of the plate 2 to engage the bone of the pelvis. The cylinders 3 may abut one another along their lengths or they may be separated along the longitudinal axis of the plate; but in either case they are parallel to each other along the plate's longitudinal axis and are centrally located on the plate.

As best shown in FIG. 3, the parallel cylinders 3 extend through the plate 2 at an angle, alpha, to the horizontal plane described by the surface of the plate 2. This angle corresponds to the angle formed by the iliac wings of the pelvis relative to the dorso-ventral plane of the human body and is between 50° and 70°, preferably 60°. The cylinders 3 are approximately 1.5 cm long and extend from the upper surface of the plate 2 a distance of about 0.6 cm and, from the lower surface of the plate 2, a distance of about 0.4 cm. The upper ends 6 of the cylinders 3 are finished to form a plane perpendicular to the longitudinal axis of the cylinders 3 while the lower ends 7 are finished to form a plane having an angle beta of 120° to the longitudinal axis. In this manner the lower ends 7 are parallel to the planar surface of the plate 2. When the plate member 1 is implanted on the pelvis, the lower ends 7 of the cylinders 3 will bear into the bone and function as guides for drilling holes through the pelvic bones to accommodate the compression rods. Alternatively, a separate jig may be used for drilling the necessary holes before the plate members are implanted.

Figure 7:
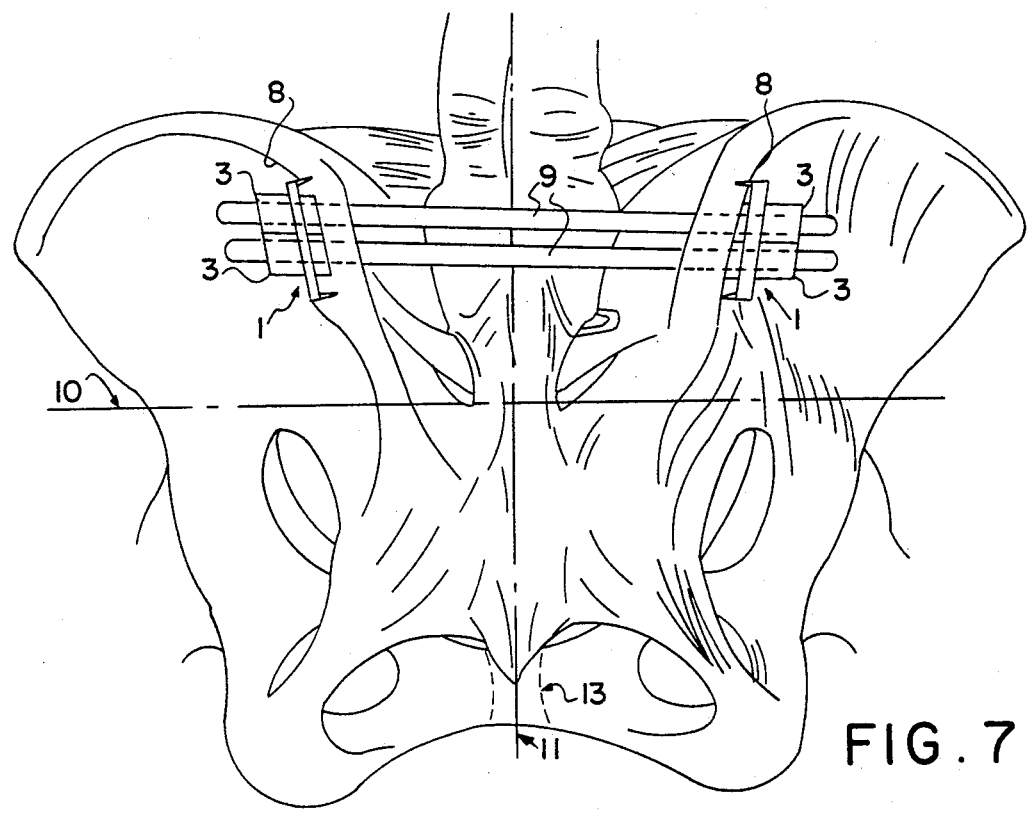
FIG. 7 is a dorsal view of the pelvis showing the plate and rod apparatus in position.
Figure 8:
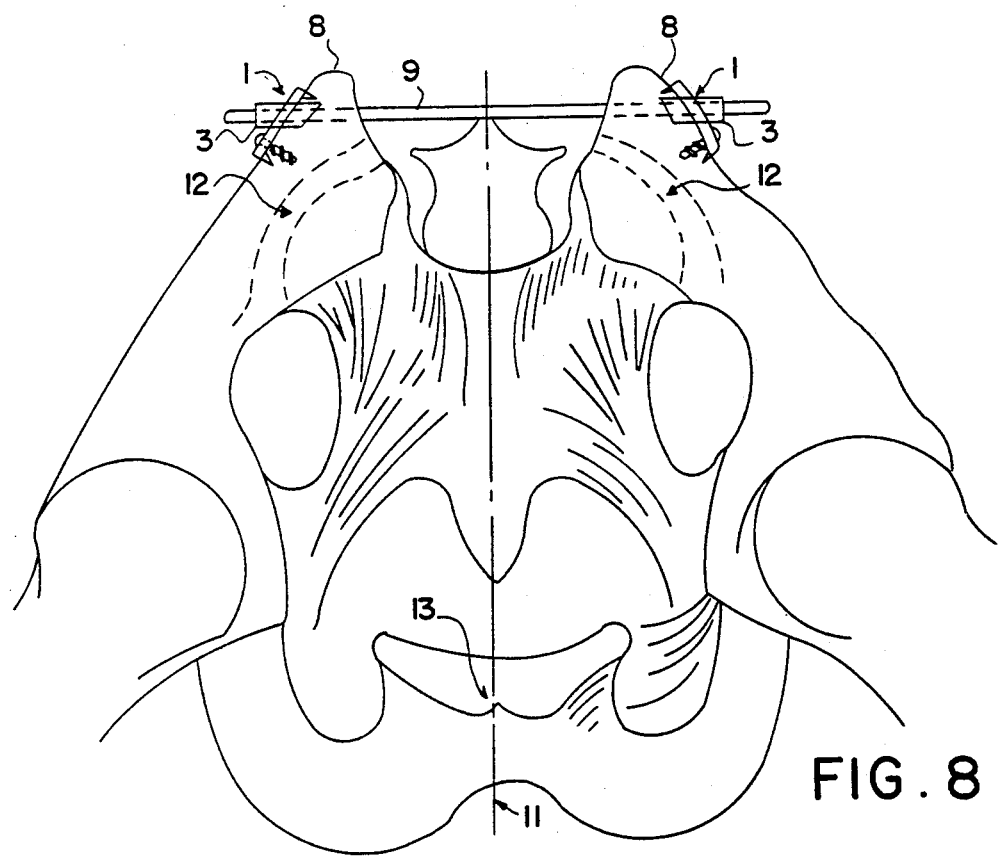
FIG. 8 is a horizontal cross-section of the pelvis showing the plate and rod apparatus in position.

The angular relationship between the cylinders 3 and the plate 2 is important to the proper fixation of the posterior pelvis, since it permits the rods employed with the plate member 1 to exert compression more evenly across the fracture or dislocation site. Turning to FIGS. 7 and 8, the posterior plate and rod apparatus is shown in position with a plate member 1 applied to the outer surface of each posterior iliac wing 8 and a pair of connecting rods 9 linking the plate members 1 and spanning the distance between the iliac wings 8. These rods 9 may be Edwards Rods or such other rods as can achieve a fixed relationship with the plate members 1 to provide a rigid fixation of the posterior pelvis. As shown, the rods 9 pass through the hollow cylinders 3 of each plate member 1 so as to be parallel. This parallel system prevents toggle and rotation between the plates and firmly stabilizes the pelvis.

As is clearly seen in FIGS. 7 and 8, the angular relationship between the parallel cylinders 3 and the plate section 2, when the plate members 1 are implanted, corresponds to the angular relationship formed by the surface of the ilium with the vertical dorso-ventral plane 11. Accordingly, when the plate members 1 are oriented with the angle α facing ventrally, the longitudinal axis of the cylinders 3 will be perpendicular to the vertical dorso-ventral plane 11 and parallel to the horizontal plane 10. In this manner, when the rods 9 are inserted, the compression forces exerted by the apparatus are more evenly applied across the site of the fracture or dislocation, for example the sacroiliac joint 12, thus reducing or eliminating any anterior opening of the symphysis pubis 13.

Figure 4:
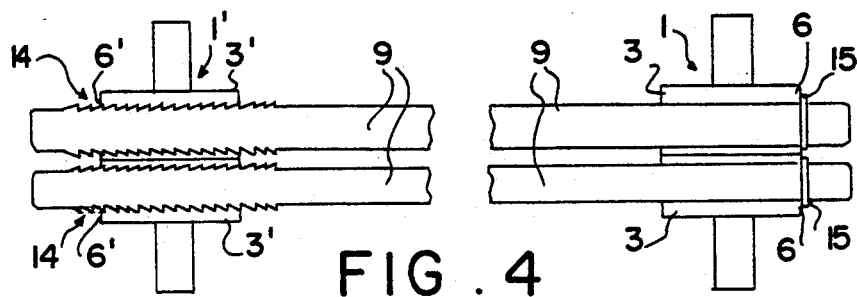
FIG. 4 is a detailed cross-section through a complete plate and rod apparatus illustrating the relationship between the rods and plates.

A fixed relationship between the rods 9 and the plate members 1 is achieved by the preferred construction illustrated in FIG. 4. One end of each rod 9 is provided along a portion of its length with a plurality of ratchet detents 14 that taper from a broad base toward the end of the rod 9. The opposite end of the rod 9 has a related securing means, in this case a C-shaped spring clip 15 of well known design that fits into a circumferential groove cut into the rod a short distance inward from the end. When the rods 9 are inserted into the cylinders 3 of one plate, the C-clips 15 abut against the ends 6 of the cylinders 3. The rods 9 traverse the space between the iliac wings entering the opposing cylinders 3, of the opposite plate member 1'. The detents 14 engage the inner surface of the cylinders 3' and, where the rods 9 exit from the cylinders 3', the broad base of the ratchet detents 14 abut against the ends 6' of the cylinders 3'. In this manner, a fixed and stable relationship is achieved between the rods 9 and the plate members 1 and 1'. The foregoing is a preferred manner of achieving a fixed relationship between the plate members 1 and rods 9. Other means or methods may be used and are within the scope of this invention.

As noted previously, double vertical fractures of the pelvis involve both a fracture or dislocation of the ilium and a fracture or dislocation of the pubic symphysis or the ischia. While ischial fractures can be pulled together and held in compression with a standard bone plate to effect union of the fractured bone, the area of the pubic symphysis is a resilient joining between the left and right ischia and exhibits some flexibility. Prior apparatus and methods employed rigid fixation means across the symphysis which negated the inherent flexibility of this union and also contributed to difficulty in obtaining accurate realignment of sacroiliac fractures or dislocations. The second part of the apparatus of this invention allows fixation of symphysial fractures or dislocations while maintaining flexibility across the union which permits surgery on the posterior ring of the pelvis without further anterior disruption.

Figures 5, 6:
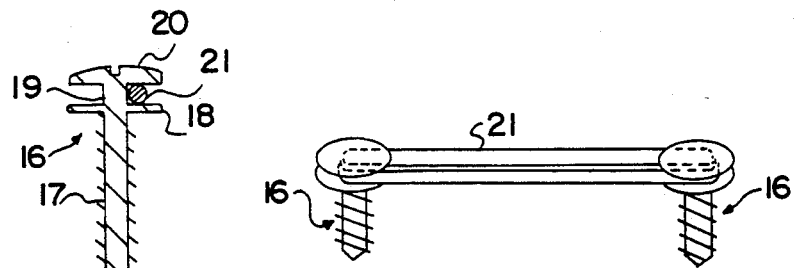
FIG. 5 is a view of the screw employed in the screw and cable apparatus of this invention.
FIG. 6 is an oblique view of the screw and cable assembly of this invention.

Referring to FIGS. 5 and 6, this part of the apparatus comprises at least two cortical screws 16, having the construction illustrated in FIG. 5, and a flexible cable, band, or the like 21 secured between two of these screws across the fracture or dislocation. The screws 16 have a construction specifically designed for this use comprising a threaded shaft 17, an intermediate flange 18, and a head 20. The head 20 has a means for engagement by an appropriate driving tool and the threaded shaft section 17 has threads of a type and dimension suitable for engagement with human bone. Between the head 20 and the intermediate flange 18 is a non-threaded shaft section 19 about which the aforementioned cable or band 21 is secured. The length of the non-threaded shaft 19, that is the distance between the upper surface of the intermediate flange 18 and the undersurface of the head 20 is equivalent to at least one thickness of the cable or band 21.

Figure 9:
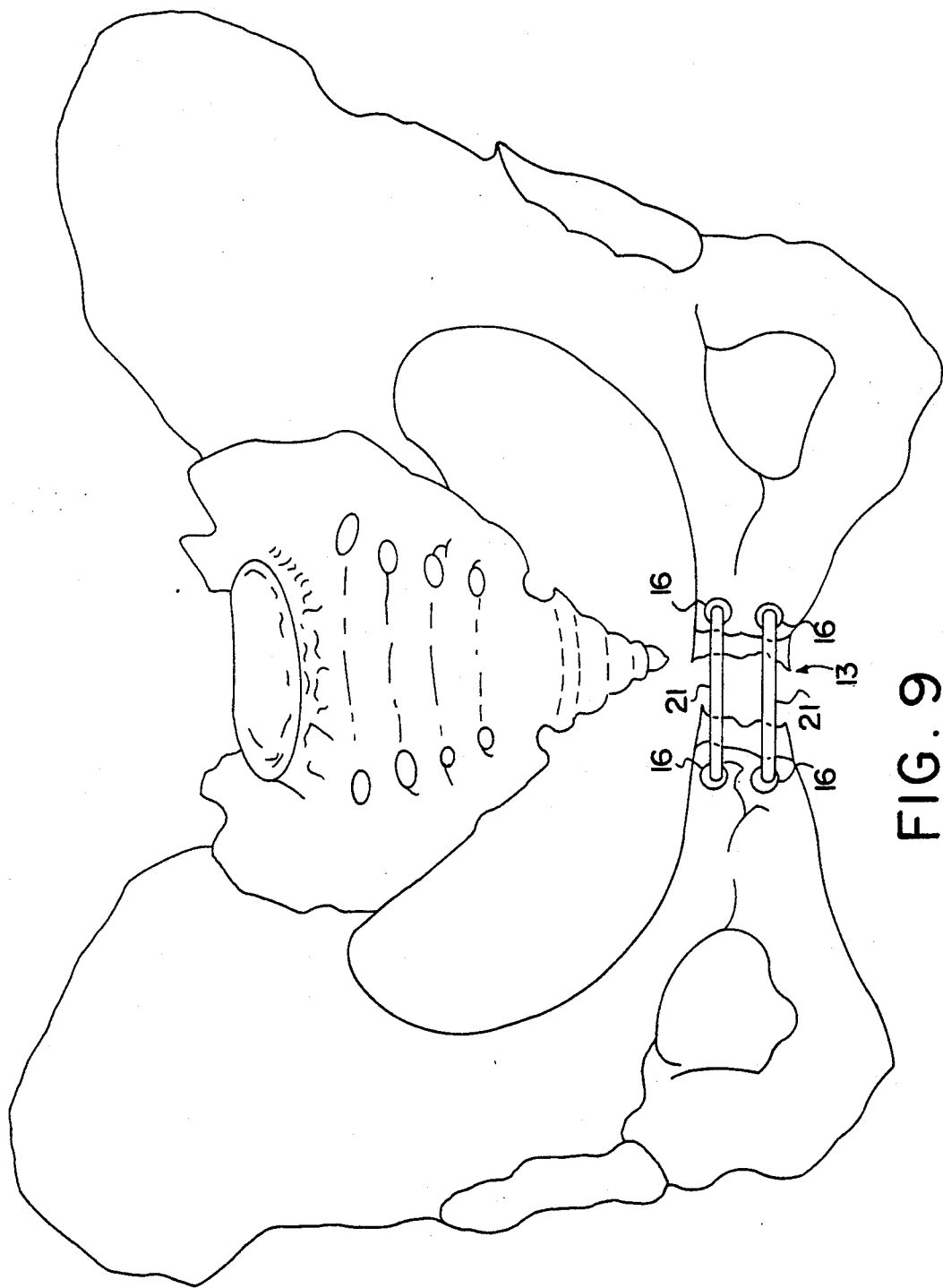
FIG. 9 is an anterior view of the pelvis showing the screw and cable apparatus in place across the ruptured pubic symphysis.

Referring to FIGS. 6 and 9, it can be seen that at least one pair of screws 16 and one cable or band 21 is employed across the pubic symphysis 13. Preferably, at least two sets of screw and cable apparatus are used. The screws 16 of each set are secured to the bone on either side of the symphysis and the cable or band 21 secured between each one. If the object is to hold the symphysis against further disruption while surgery is performed on the related posterior fracture, then the cable or band 21 may be a preformed continuous loop of an appropriate length to maintain the disruption. Alternatively, if the object is to draw the ischia together and thereby close a complete fracture or disruption of the pubic symphysis 13, then a continuous loop of smaller dimension may be used or the cable or band 21 may be a non-continuous strand of wire or the like that is wrapped around opposing screws and then tightened to draw the ischia together, then tied or otherwise secured to prevent their pulling apart. As with the posterior plates and rods, the screws 16 and cable or band 21 should be manufactured from biocompatible materials.

The preferred operative method employing the apparatus described herein above is broadly a two-step procedure involving, first, securing the anterior pubic symphysis from further disruption with the screw and cable materials and, second, fixation of the posterior fracture or disruption with the plate and rod apparatus. Prior or subsequent to the posterior fixation, the anterior pubic symphysis may, if disruption thereof is complete, be fully reduced by means of the screw and cable apparatus.

The method and apparatus herein described is one preferred embodiment of the present invention and it will be understood that changes in details may be resorted to which will fall within the scope of the invention as claimed.

What is claimed is:

1. An apparatus for stabilization and reduction of pelvic fractures comprising in combination an anterior fracture stabilization apparatus comprising at least two cortical attachment members and a uniting means to unite said members, and a posterior fracture stabilization apparatus comprising at least two plate members attachable to opposing posterior iliac wings of a human pelvis, at least two receiving means on each of said plate members and at least two substantially straight connecting rods receivable in each of said receiving means for connecting said plate members across the intervening sacro-iliac space of the human pelvis, said connecting rods having means for achieving a fixed and stable relationship with said receiving means and providing compressive force to said pelvis via said plate members.

2. The apparatus of claim 1 wherein said cortical attachment members comprise screws having a head, a shaft with a threaded portion extending from a point distal of said head to a distal end of said shaft, and an intermediate, non-threaded portion for engaging said uniting means.

3. The apparatus of claim 2 wherein the intermediate non-threaded portion of said screws comprises an intermediate annular flange located on the shaft of said screws immediately adjacent the proximal end of said threaded portion and distally spaced from said head a sufficient distance to accommodate said uniting means between said head and said flange.

4. The apparatus of claim 3 wherein said uniting means comprises a continuous loop of flexible, non-resilient material of a thickness to be accommodated within the area of said screw defined by said head and said flange.

5. The apparatus of claim 3 wherein said uniting means comprises an elongated strand of flexible material having a thickness to be accommodated within the area of said screw defined by said head and said flange.

6. The apparatus of claim 1 wherein said posterior stabilization apparatus comprises two plate members and two substantially straight connecting rods, wherein each of said plate members comprises a plate having fixation means and said receiving means for receiving said connecting rods, with said receiving means comprising two hollow cylinders substantially centrally located on said plate and arranged parallel to each other and to the longitudinal axis of said plate.

7. The apparatus of claim 6 wherein said cylinders extend through said plate at an angle of 50° to 70° to the planar surface of said plate and have at least 40% of their length on one side of said plate.

8. The apparatus of claim 7 wherein said cylinders extend through said plate at an angle of 60° to the planar surface of said plate.

9. The apparatus of claim 7 wherein the ends of said cylinders to contact bone are finished such as to be parallel to the surface of said plate and the opposite ends of said cylinders are finished such as to be perpendicular to the longitudinal axis of said cylinders.

10. The apparatus of claim 6 wherein said fixation means comprises sharpened spines extending from one surface of said plate.

11. The apparatus of claim 6 wherein said connecting rods comprise substantially straight elongate rods having along a portion of the length of one end thereof a plurality of ratchet detent members and, at the opposite end thereof, means to secure said rods against said cylinders.

12. An apparatus for the stabilization and reduction of double vertical fractures of the pelvis comprising an anterior stabilization apparatus and a posterior stabilization apparatus;

said anterior stabilization apparatus comprising at least two cortical screws and a uniting means wherein said screws have a non-threaded shaft portion adjacent a head thereof defining an area of sufficient width and depth to accommodate said uniting means, said uniting means comprising an elongated, flexible, non-resilient material of sufficient length to span at least twice the distance between said screws when said screws are implanted on opposite sides of a fracture; and said posterior stabilization apparatus comprising two planar, plate members, each plate member having at least two elongated hollow cylinders extending therethrough at an angle of 60° to the plane of the plate member, said cylinders being arranged parallel to each other along the longitudinal axis of said plate member, said plate member having fixation means for attachment to pelvic bones, and further comprising two substantially straight elongated connecting rods for accommodation within said cylinders and having means for fixedly securing said rods within said cylinders comprising ratchet detent means along the length of one end of said rods and removable cylinder face abutting means at the opposite end of said rods.

13. A method for treating double vertical fractures of the anterior pubic symphysis and the posterior sacral-iliac portion of the pelvis comprising;

stabilizing the anterior pubic symphysis with a flexible fixation means comprising cortical screws having a shaft portion adapted to accommodate an elongate flexible non-resilient uniting means wherein at least one screw is implanted into the pelvic bone on opposite sides of the anterior pubic symphysis and said opposing screws are bound together by said uniting means such that said uniting means spans said pubic symphysis; and stabilizing the posterior sacral-iliac fracture with a rigid fixation means comprising two planar plate members, each plate member having receiving means thereon, and two elongate, substantially straight fixation rods receivable in said receiving means and having means for being fixedly secured to said plate members via said receiving means, wherein said plate members are affixed, one each, to the outer surface of the iliac wings of the pelvis in the vicinity of the posterior, superior spine thereof, with said rod receiving means extending through said pelvic bone, said plate members being horizontally opposed when in place, and inserting said fixation rods into said receiving means of one of said plate members, through said pelvic bone and across the sacral space to the receiving means of the second plate member and securing same therein such that said rods span the space between the iliac wings dorsal of the sacrum to thereby apply compression across the sacroiliac fracture.

* * * * *